United States Patent
Velazquez Pereda et al.

(10) Patent No.: US 8,716,506 B2
(45) Date of Patent: May 6, 2014

(54) XYLITOL ESTERS AND ETHERS APPLIED AS ALTERNATIVE EMULSIFIERS, SOLVENTS, CO-EMULSIFIERS AND PRESERVATIVE SYSTEMS FOR PHARMACEUTICAL AND COSMETIC PRODUCTS

(75) Inventors: Maria Del Carmen Velazquez Pereda, Sao Paulo-Sp (BR); Marcio Antonio Polezel, Indaiatuba-Sp (BR); Gustavo Campos Dieamant, Sorocaba-Sp (BR); Cecilia Nogueira, Sorocaba-Sp (BR); Lilian Mussi, Sorocaba-Sp (BR); Marcos Roberto Rossan, Sorocaba-Sp (BR); Carlos Roque Duarte Correia, Campinas-Sp (BR); Nilton Soares Camilo, Campinas-Sp (BR)

(73) Assignee: Chemyunion Quimica Ltda., Sorocaba (BR)

( * ) Notice: Subject to any disclaimer, the term of this patent is extended or adjusted under 35 U.S.C. 154(b) by 0 days.

(21) Appl. No.: 12/998,437

(22) PCT Filed: Oct. 20, 2008

(86) PCT No.: PCT/IB2008/054321
§ 371 (c)(1),
(2), (4) Date: Jun. 20, 2011

(87) PCT Pub. No.: WO2010/046726
PCT Pub. Date: Apr. 29, 2010

(65) Prior Publication Data
US 2011/0251415 A1    Oct. 13, 2011

(51) Int. Cl.
*A23D 9/00* (2006.01)
*C07C 43/00* (2006.01)

(52) U.S. Cl.
USPC .......................................... 554/227; 568/680

(58) Field of Classification Search
USPC .......................................... 554/227; 568/680
See application file for complete search history.

(56) References Cited

U.S. PATENT DOCUMENTS 4,966,754 A   10/1990  Purohit et al.
5,306,733 A *  4/1994  Adamski et al. ................ 521/63

(Continued)

FOREIGN PATENT DOCUMENTS

DE    42 37 081     5/1994
DE    195 41 967    5/1997

(Continued)

OTHER PUBLICATIONS

The response to the Austrian Office Action presented on May 27, 2011.

(Continued)

*Primary Examiner* — Deborah D Carr
(74) *Attorney, Agent, or Firm* — Collard & Roe, P.C.

(57) ABSTRACT

This patent application has as purpose the application/utilization of esters and ethers derived from xylitol, obtained by organic synthesis, as alternative emollient, moisturizing, emulsifier and co-emulsifier and preservatives for pharmaceutical, cosmetic and veterinarian products. The molecules required in this invention patent are mainly xylitol esters and ethers associated to the chains of fatty acids and alcohols (FIGS. 1 and 2), applied isolated or in association with other molecules of known preserving and/or moisturizing/emollient actions, such as phenoxyethanol, butylene glycol, glycerin, caprylyl glycol, ethyl hexyl glycerin, phenetyl alcohol, nisin, lactoferrin, among others, as well as in association with other emollient/moisturizing and preservatives for application in cosmetic, pharmaceutical and veterinarian formulations. Some of these associations and isolated applications present important antimicrobial action, such as for example, inhibiting the growth of *Escherichia coli*, *Pseudomonas aeruginosa*, *Staphylococcus aureus*, *Aspergilus niger* and *Candida albicans*. Also, the present co-emulsifier, emollient, solving and moisturizing properties.

2 Claims, 5 Drawing Sheets

(56) References Cited

U.S. PATENT DOCUMENTS

| | | | |
|---|---|---|---|
| 5,648,067 A | 7/1997 | Dillenburg et al. | |
| 6,391,863 B1 | 5/2002 | Philippe et al. | |
| 6,447,793 B2 | 9/2002 | Aust et al. | |
| 2002/0192257 A1 * | 12/2002 | Farone et al. | 424/405 |
| 2006/0110415 A1 | 5/2006 | Gupta | |

FOREIGN PATENT DOCUMENTS

| | | | |
|---|---|---|---|
| DE | 196 31 003 | | 2/1998 |
| EP | 0 775 478 | | 5/1997 |
| FR | 2 722 199 | | 1/1996 |
| FR | 2 728 257 | | 6/1996 |
| FR | 2728257 A1 * | 6/1996 | C07C 69/30 |
| GB | 1016885 * | | 8/1963 |
| GB | 1 016 885 | | 1/1966 |
| JP | 03-247229 | | 11/1991 |
| JP | 04-337397 | | 11/1992 |
| JP | 08-283139 | | 10/1996 |
| JP | 11-209260 | | 8/1999 |
| SU | 371 202 | | 2/1973 |
| SU | 371202 * | | 2/1973 |
| WO | WO 97/12597 | | 4/1997 |
| WO | WO 01/82926 | | 11/2001 |
| WO | WO 02/47645 | | 6/2002 |

OTHER PUBLICATIONS

International Search Report, May 2011.

* cited by examiner

XYLITOL ESTERS AND ETHERS APPLIED AS ALTERNATIVE EMULSIFIERS, SOLVENTS, CO-EMULSIFIERS AND PRESERVATIVE SYSTEMS FOR PHARMACEUTICAL AND COSMETIC PRODUCTS

INTRODUCTION

This patent application has as purpose the application/utilization of esters and ethers derived from xylitol, obtained by organic synthesis, as alternative emollient, moisturizing, emulsifier and co-emulsifier and preservatives for pharmaceutical, cosmetic and veterinarian products. The molecules required in this invention patent are mainly xylitol esters and ethers associated to the chains of fatty acids and alcohols (formulas 1 and 2), applied isolated or in association with other molecules of known preserving and/or moisturizing/emollient actions, such as phenoxyethanol, butylene glycol, glycerin, caprylyl glycol, ethyl hexyl glycerin, phenetyl alcohol, nisin, lactoferrin, among others, as well as in association with other emollient/moisturizing and preservatives for application in cosmetic, pharmaceutical and veterinarian formulations. Some of these associations and isolated applications present important antimicrobial action, such as for example, inhibiting the growth of *Escherichia coli, Pseudomonas aeruginosa, Staphylococcus aureus, Aspergilus niger* and *Candida albicans*. Also, the present co-emulsifier, emollient, solving and moisturizing properties.

n = 1 a 22;

R = [H, CH$_3$, —CH$_2$CH$_3$, —CH$_2$(CH$_2$)$_y$—CH$_3$ with y = 1 to 15]

n=1a22; R=[H, CH$_3$, —CH$_2$CH$_3$, —CH$_2$(CH$_2$)$_y$—CH$_3$ with y=1 to 15]

PRIOR ART

Some compounds related or similar to xylitol esters molecules were developed:

FR2728257—Preparation of glycerol and xylitol monoesters as emulsifiers and liquid crystals.
US2006110415—Topical delivery system comprising esters of hydroxy acids for cosmetic and pharmaceutical agents.
JP04337397—Surfactant compositions for liquid detergents and hair-care products.
JP03247229—Emulsifiers of hexose fatty acid monoesters and long chain fatty acid monoglycerides as foaming agents for cakes.
FR2722199—Synthesis of valproic acids-substituted sugars as hypnotics and anticonvulsants.
WO2001082926—Manipulation of oxidative phosphorylation for hypersensitizing tumor cells to glycolytic inhibitors.
WO2002047645—Cosmetic composition containing 7-hydroxy DHEA and/or 7-keto DHEA and at least a peeling agent.
JP11209260—Cosmetics containing diglycerin monofatty acid esters.
DE19631003—Combinations based on partial glycerides and dialkyl-substituted acetic acids active against bacteria, mycota, and viruses.
EP775478—Bactericidal, fungicidal, and antiviral combinations of partial glycerides and dialkyl-substituted acetic acids for use in cosmetic and dermatological compositions.
DE 19541967—Antibacterial, antifungal, and antiviral combinations of partial glycerides and aryl compounds.
WO9712597—Use of carbohydrates for promoting skin exfoliation.
JP08283139—Moisturizing and rough skin-preventing cosmetic containing hydroxycarboxylates.
DE 4237081—Deodorizing cosmetics containing di- and triglycerol esters.

Some Compounds as Alternative Preservatives were Developed:

U.S. Pat. No. 6,447,793—Water soluble, broad spectrum preservative system for cosmetic and personal care products.
U.S. Pat. No. 4,966,754—Essential oils as preservative for cosmetic compositions.

BACKGROUND OF THE INVENTION

This invention patent has the purpose of application/utilization of esters and ethers derived from xylitol, obtained by organic synthesis, as alternative emollient, moisturizing, co-emulsifier and preservatives for pharmaceutical, cosmetics and veterinarian products. The molecules to be patented are mainly the xylitol esters and ethers associated to the chains of fatty acids and alcohols and Trixylitol Phosphate and, applied isolated or in association with other molecules with known preserving and/or moisturizing/emollient action, such as phenoxyethanol, butyleneglycol, caprylylglycol, ethylhexylglycerin, as well as in association with other emollient/moisturizing and preservatives for application in cosmetic, pharmaceutical and veterinarian products. Some of these isolated associations and applications present important antimicrobial action, such as for example, inhibition of the growth of *Escherichia coli, Pseudomonas aeruginosa, Staphylococcus aureus, Aspergilus niger* and *Candida albicans*. Also, presented co-emulsifier, emollient, solving and moisturizing properties.

DETAILED DESCRIPTION OF THE INVENTION

This patent application aims to the application/utilization of ethers and esters derived from xylitol, obtained from organic synthesis, as alternative emollient, moisturizing, co-emulsifier and preservatives for pharmaceutical, cosmetic and veterinarian products. The molecules to be patented are mainly the xylitol esters and ethers associated to the chains of fatty acids and alcohols and trixylitol phosphate, applied isolated or in association with other molecules with known preserving and/or moisturizing/emollient action, such as phenoxyethanol, butylene glycol, caprylyl glycol, ethyl hexyl glycerin, as well as in association with other emollient/moisturizing and preservative agents for application in cosmetic, pharmaceutical and veterinarian formulations. Some of these isolated associations and applications presented important antimicrobial action, such as for example, inhibiting the growth of *Escherichia coli, Pseudomonas aeruginosa, Staphylococcus aureus, Aspergilus niger* and *Candida albicans*. Also, they presented co-emulsifier, emollient, solving and moisturizing properties.

Preserving of Pharmaceutical, Cosmetics and Veterinarian Products

Cosmetics, toilet, perfume and cleaning products, as well as medicines and other pharmaceutical consumables, shall be duly preserved for withstanding the processes of manufacture, storage, handling by the consumer and consequent maintenance of the health integrity of the user. The contamination during the process of manufacturing the product may be controlled, however, the handling and particularly the incorrect use by the consumer may promote microbial growth. Microbial contamination presents a potential risk for the quality of the product and may cause the separation of the emulsified phases, change in color, production of gases and odors, but, above all, affect the health of the consumer, some incidents have already been reported, such as infection by *Klebsiella pneumoniae* in hand cream and *Pseudomonas* in eyelash mascara.

The preservative agents shall be bioactive molecules effectively acting with the destruction or inhibition of microorganism growth. For this reason, the action spectrum and the used concentration shall be accurately calculated to assure the integrity of the product. The ideal preservative agent shall be stable, compatible with the other ingredients of the formulation, have a with action specter in low concentration and be active in a large range of pH, besides not causing toxic, irritating and hypersensitizing effects. However, few agents approximate this ideal, and all, without exceptions, have demonstrated causing contact sensitizing. Table 1 shows the main preservative agents used in cosmetics and pharmaceutical products.

The presence of preservative agents in cosmetic compounds is obviously necessary, however, it is essential to consider the potential health hazards associated to the use of the same.

The exposure to a preservative agent may occur by ingestion, inhalation or skin permeation, however, since this is a biologically active molecule, simply the contact with the skin may cause contact irritation or sensitizing. It is estimated that approximately 12% of the population presents adverse effects to cosmetics, particularly allergic reactions, the preservative agents being in second place in this ranking, behind only of the fragrances.

TABLE 1

Preservative agents used in cosmetic preparations

| | Usual Concentrations (%) |
|---|---|
| Parabens | |
| Methylparaben | |
| Ethylparaben | 0.1-1 |
| Propylparaben | |
| Butylparaben | |
| Formaldehyde and formaldehyde releasers | |
| Formaldehyde (methanal) | 0.1-0.2 |
| Quaternium-15 | 0.02-0.3 |
| Imidazolidinyl urea | 0.03-0.2 |
| Diazolidinyl urea | 0.1-0.5 |
| 2-bromo-2-nitropropane-1,3-diol (bronopol) | 0.01-1 |
| 1,3-Dimethylol-5,5-dimethyl hydantoin (DMDM hydantoin) | 0.1-1 |
| Isothiazolinones | |
| Methylchloroisothiazolinone (MCI) | |
| Methylisothiazolinone (MI) | 0, 1 |
| Benzothiazolinone | 50 ppm |
| Phenoxyethanol | 1 |
| Phenoxyethanol + Methyldibromo glutaronitrile | 0.0075-0.06 |
| Potassium Sorbate | 0.6 |
| 3-iodo-2-propynyl-butylcarbamate (IPBC) | 0.1 |

The preservative agent class mostly used in cosmetics is the family of alkyl esters of para-hydroxybenzoic acid and includes methylparaben, ethylparaben, propylparaben and butylparaben. These compounds were introduced in the 1930s in cosmetic, food and pharmaceutical industry. Due to the different specter of action and solubility, these compounds are applied in association, methyl/ethylparaben mix being the most widely used. The parabens are more effective against fungus and Gram-positive bacteria and for this reason, are also associated to other preservative agents as releasers of formaldehyde, isothiazolinones and phenoxyethanol. The use of parabens in topic medicines is being discontinued due to studies demonstrating its hypersensitizing action. In spite of the parabens already being in the market for almost 80 years and demonstrating, in general, stability, efficacy and safety, the studies show that these compounds may cause sensitizing reactions, particularly in individuals who present dysfunction in the skin barrier, such as traumas or eczema.

Another group of widely used preservative agents, since 1889, are the formaldehydes and releasers of formaldehyde.

These compounds are probably the most problematic in terms of allergies and include DMDM hydantoin, imidazolidinyl urea, diazolidinyl urea, bronopol and quaternium-15, this last one being the main cause for cosmetic allergy in the USA. Free formaldehyde in cosmetics is falling out of use due to its potential for irritating, hypersensiting and carcinogenic properties, being forbidden in countries like Japan and Sweden. Its use in aerosols is forbidden in the USA and Brazil. The compounds releasing formaldehyde have been replacing the use of free formaldehyde, however this is still found in shampoos, nail polish and strengthener. These compounds have a molecule of formaldehyde in their chemical structure, which is easily released and may cause allergic reactions and also interact with other substances producing nitrosamines that are known carcinogenic agents.

Clinical tests reveal that formaldehyde causes contract hypersensitizing in 1-9% of the assessed volunteers, even in concentrations of 30 ppm of free formaldehyde. Quaternium-15 is the preservative agent of this category with the larger potential for donating formaldehyde. A solution at 0.1% is able to generate 100 ppm of free formaldehyde. Imidazolidinyl urea was introduced in 1970 and quickly became the second mostly used preservative agent, over passed only by the parabens. The sensitizing caused by imidazolidinyl urea is due to the whole molecule and not the release of formaldehyde. Diazolidinyl urea, launched in 1982, has a larger action specter than imidazolidinyl urea, however, it has more irritating potential. Bronopol is used in shampoos and emulsions in the concentration of 0.2%, which may reach the equivalent to 30 ppm of free formaldehyde and cause contact dermatitis. The use of this compound has been falling during the last 15 years. DMDM hydantoin has 2% of free formaldehyde and is the compound of this class with the larger action specter and widely used in shampoos. De Groot and collaborators demonstrated that 57% of the volunteers presented hypersensitivity to the contact test with this compound. Bronopol was replaced in various topic medicines destined to sensitive skin, since causes acute and sever dermatitis when applied.

A preservative system commonly used in moisturizing creams, shampoos and makeup is the mix of methylchloroisothiazolinone with methylisothiazolinone (MCI/MI) in the ratio of 3:1, respectively. This system is effective in low concentrations against a wide variety of fungus, yeasts and bacteria (gram positive and negative), but it also is irritating in concentrations over 200 ppm. Tests with animals have revealed that this class of preservative agents is potentially allergenic, MCI with more intensity. There are over 100 publication reporting allergy to the association MCI/MI. A typical example is women who present dermatitis in the hands or face, particularly in the eyelids. Most of the cosmetics responsible for the contact dermatitis allergic to this association are the leave-on products. Also reported is the dermatitis in buttocks and perineum region due to the presence of this compound in toilet paper. The allowed levels of MCI/MI in cosmetics are maximum 0.1% (15 ppm of product ingredients) in Brazil, USA, Canada, Europe and Japan. However, for leave-on products in USA and Canada only 7 ppm are allowed for using.

Phenoxyethanol is a widely used preservative agent for toilet products and has a wide antimicrobial specter against gram positive and negative bacteria, mold and yeasts. Phenoxyethanol contains phenol with an important effect inhibiting phagocytosis, thus reducing the efficiency of the primary immunologic answer. This compound is also used in vaccines and may cause systemic poisoning, headache, shock, debilitation, convulsions, kidney and cardiac damage. Phenoxyethanol may also contain ethylene oxide waste that is a potential agent for causing dermatitis, burns, blisters and eczemas.

Phenoxyethanol is also used in association with methyldibromo glutaronitrile (MDBGN) in a ratio of 4:1. In North America, the use of this association is restricted to bath product and cosmetics in a concentration of 0.0075-0.06%. In Europe, this association has been widely used as substitute for the one consisting of MCI/MI. in spite of this, allergic reactions to the association of phenoxyethanol/MDBGN have been described, particularly due to the presence of MDBGN. Most cases present a contact dermatitis in the hands, severe, acute and with blisters, also in the face, genitals and extremities. MDBGN is not allowed in Japan.

Potassium sorbate is another active preservative agent against fungus and yeasts, but with small effect against bacteria. Another disadvantage of the potassium sorbate is that its activity depends on the pH, this activity is reduced with pH less than 4.5. Some studies have demonstrated that, in clinical tests of skin irritation and sensitizing, potassium sorbate caused rashes and edema.

3-iodo-2-propynyl-butylcarbamate (IPBC) is a halogen compound with effective action against fungus, bacteria and parasites. The use of IPBC in the cosmetic industry has been increasing since it has low toxicity and low sensitizing risk. However, some allergic reactions have been reported.

Alternative Preservative Agents with Lower Toxicity Risk

Considering that the preservative agents available in the market present, without exceptions, some risk of hypersensitivity, efforts have been directed to developing natural compounds with antimicrobial activity with the purpose of reducing or even replacing the traditional preservative agent.

Among these compounds, vegetal derivates are widely used, due to their antimicrobial properties and for this reason have been proposed as alternative preservative agents instead of synthetic agents. Alkaloids, steroids, flavonoids, cumarins, quinones, phenolic and polyphenolic compounds, glycoprotein, carbohydrates, terpenes and a wide variety of essential oils have demonstrated important antimicrobial activity. The essential oils, in spite of presenting antimicrobial potential, produce hypersensitizing reactions, especially photo-allergy, when applied on the skin, limiting their use as preservative agents in products destined to topic application. The essential oils that have more documented due to the allergen potential are: tea tree, lavender, jasmine, lemon, orange, citronella, *cassia*, ylang-ylang, *aniba rosaeodora*, and clover oils.

Other natural or semi-synthetic compounds have been developed in an attempt to obtain safer and more efficient molecules for preserving food, pharmaceutical and cosmetic products. Among them, are the derivates of sugar, fatty acids and aminoacids, which present excellent biological compatibility, besides presenting, in cosmetic and dermatologic preparations, other adjuvant properties that help obtaining more stable formulations, such as for example, emollient, moisturizing, solving and co-emulsifier properties.

The antimicrobial activity of monoesters of fatty acids is conditioned to the presence of some hydrophilic group in the molecule. Event though the esters of fatty acids with monohydrate alcohols are not effective against microorganisms, esters alpha-hydroxy-fatty acids with monohydrate alcohols and esters of de fatty acids with polyhydrate alcohols have active biological activity. The saccharose esters, such as for example, of lauric acid, has shown to be active against Gram positive, negative bacteria and fungus. However, studies have demonstrated that the diesters of saccharose are more powerful than the monoesters.

Sugars also have an important role in the sensorial, physical and chemical properties of food, cosmetics and medicines. Saccharose has three hydroxymethyl groups available for esterification that may determine the formation of lipophylic or hydrophilic surfactants. This process may be conducted without using ethylene oxide, which makes the molecule less irritating. For this, the absence of ethylene oxide, the as characteristics of solubility, compatibility with other preservative agents and the low allergenic potential, make the saccharose esters to be potential agents for preventing the microbial contamination (Kabara and Orth, 1997). Lauric, stearic and acetylated stearic acids may be used in the saccharose esters, being reported a bacteriostatic action against Gram positive bacteria and less against Gram negative bacteria. Lerk and Sucker studied the saccharose laureate on *E. coli, P aeruginosa* and *S. aureus* and found an important role in the preservation of liquid oral preparations (Lerk and Sucker, 1993).

A market example, that presents a strong impact in the area of cosmetic and dermatologic products is SENSIVA® SC-10 (Schülke & Mayr, Norderstedt, Germany), which consists of a mix of ethylhexylglycerin (octoxyglycerin) and caprylyl glycol, may be used as emollient and moisturizing, besides contributing to the microbiologic stability of the formulation. Another market product used with the same purpose is LIPACIDE®C8G (Seppic, Paris, France) consisting of capryloyl glycine. It is important to mention that these compounds presented excellent coadjuvant activities of formulation, absence of allergenic and irritating potential, but do not have antimicrobial activity able to replace the preservative agents of the product, allowing only the reduction of the concentration of the same. In accordance with the GNPD (Global New Products Database), these two excipients are found in approximately 155 and 385 cosmetic products, respectively.

Xylitol and Derivates

Another sugar with important antimicrobial properties describe in the literature is xylitol. Xylitol is an alcohol derived from sugar that contains five carbons in its chain, occurs naturally in some fruits and has been widely used as sweetener for chewing gum. Studies have demonstrated that xylitol in a concentration of 5% inhibited the growth of *Streptococcus pneumoniae* and reduced the adherence levels of the otopatogens *S. pneumoniae* and *Haemophilus influenzae* in the epithelial nasopharyngeal cells. Xylitol is also widely studied for inhibiting the growth of *S. mutans*, the main agent causing dental caries. The action mechanism by which xylitol inhibits the growth of microorganisms seems to be related with the fructose phosphotransferase system responsible for carrying xylitol into the prokaryotic cell, where it is not totally metabolized leading to the destruction of the same. The xylitol molecule, in spite of all the above described characteristics, is not able to promote, all by itself, the complete preservation of a formulation. Also, high application concentrations do not allow its use as main preservative agent of the system.

These affirmations are supported with efficacy tests in vitro for attesting the antimicrobial action (preserving), as well as tests of application in cosmetic formulation, in order to attest the co-emulsifier, emollient/moisturizing and solving properties according to the examples described below.

EXAMPLE 1

Determination of Minimum Inhibitory Concentration (MIC) of Xylitol Esters, Isolated or in Association with Other Preservative Compounds.

This study evaluated the lowest concentration of the molecules C8-Xylitol and C8-2,6-Xylitol or the association of this molecules with phenoxyethanol that will inhibit the visible growth of a microorganism comparing to results obtained to some molecules that have been used as preservative system.

The concentration range evaluated to determine the Minimum Inhibitory Concentration (MIC) for *Staphylococcus aureus* (ATCC 6538), *Pseudomonas aeruginosa* (ATCC 13388) and *Escherichia coli* (ATCC 25922) microorganisms using the Mueller-Hinton medium and *Candida albicans* (ATCC 10231) and *Aspergillus niger* (CCT 1435) microorganisms using RPMI 1640 medium was from 0.01 to 20.0 mg/mL of pure molecule. For a better evaluation of the results obtained with the samples, Minimum Inhibitory Concentrations (MIC) of the solvents used in this test were also determined. All the tests were performed according CLSI (NC-CLS) microbiological standards.

Solutions were prepared according description on Table 1.

TABLE 1

Samples and solvents used in test of Minimum Inhibitory Concentrations (MIC)

| Molecule | Sample Solution Concentration and Solvent | Stock Solution Sample Concentration and Solvent | Control Concentration |
|---|---|---|---|
| C8-Xylitol Capryloyl Glycine | 100 mg/mL in butylene glycol or phenoxyethanol | 80 mg/mL of Sample Solution in butylene glycol | 80 mg/mL of butylene glycol or 13:87 % w/w phenoxyethanol: butylene glycol in culture medium |
| C8-2,6-Xylitol Caprylyl Glycol Ethylhexylglycerin Commercial blend of Caprylyl Glycol/ Phenoxyethanol | 400 mg/mL in butylene glycol or phenoxyethanol | 80 mg/mL of Sample Solution in butylene glycol | 80 mg/mL of butylene glycol or 78:22 % w/w phenoxyethanol: butylene glycol in culture medium |

Inoculum solution was prepared from a overnight colonies suspension diluted in sterile saline solution; which was the optical density at 625 nm adjusted with 0.5 MacFarland standard to an absorption between 0.08 and 0.1 to bacteria and *C. albicans* and 0.09 and 0.11 to *A. niger*; following by the dilution to $10^4$ CFU/mL.

To determine MIC, each microorganism and sample was treated separately as described: 100 µL of medium was transferred to a well in a 96-well plate, following by the addiction of 100 µL of sample and homogenization of the mixture. 100 µL of the preceding mixture was taken and added to the succeeding well, which was previously load with 100 µL of medium, this new mixture was homogenized. The same procedure was made to the subsequent five wells. After the dilution process, each well received 100 µL of inoculum. A control plate of microbial agent was prepared adding 100 µL of medium and 50µL, of sample in a well. A control plate without microbial agent was also prepared.

The plates was sealed and incubated at 36° C., for 24-48 hours. After the incubation period, bacteria MIC was determined adding 50 µL of TTC (2,3,5-Triphenyl-2H-tetrazolium chloride) solution and incubating for 3 hours. MIC was defined as the lowest sample concentration capable to hinder red coloration, conferred to medium when the cells present respiratory activity. To *C. albicans* and *A. niger*, MIC was verified, after the incubation period, by changing in RPMI 1640 medium coloration from pink to yellow, which means pH change caused by microbiological growing.

Figure 1:
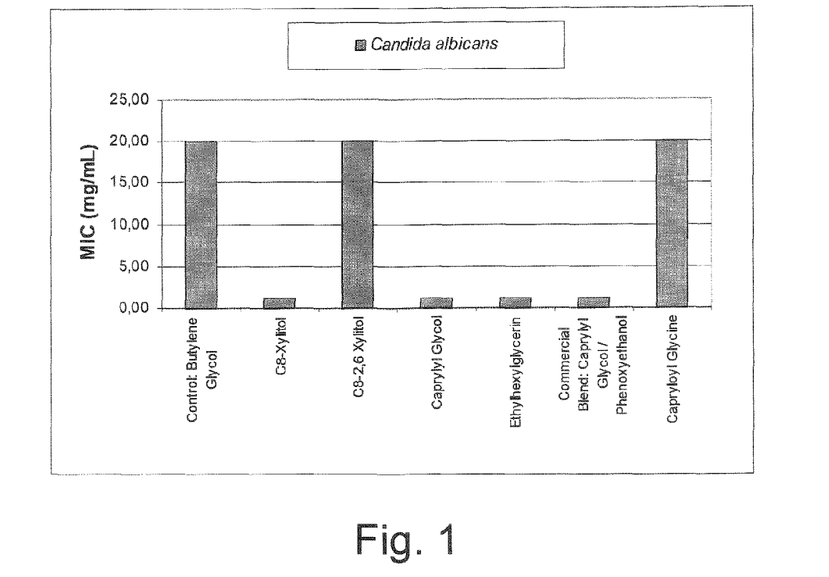
FIG. 1—shows the graph to pure molecule and respective solvent (Control) for *Staphylococcus aureus*
Figure 2:
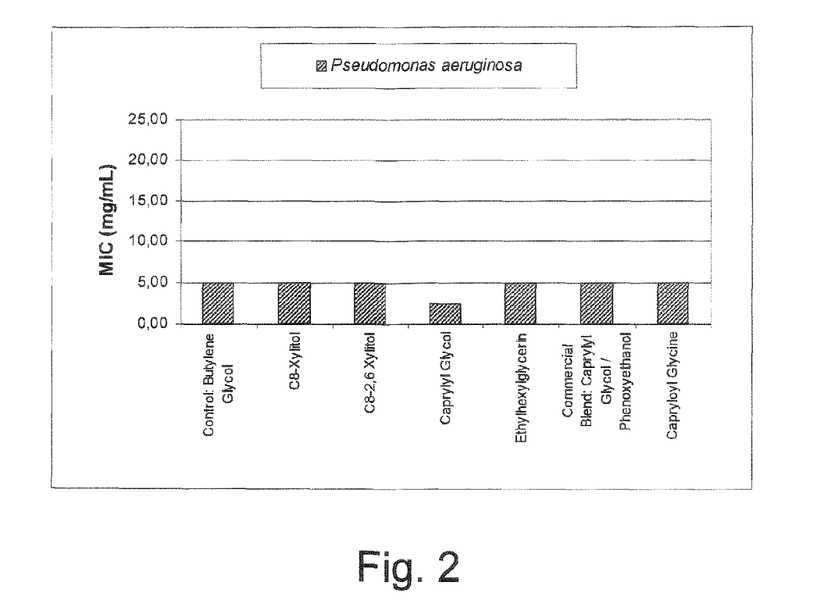
FIG. 2—shows the graph to pure molecule and respective solvent (Control) for *Pseudomonas aeruginosa*
Figure 3:
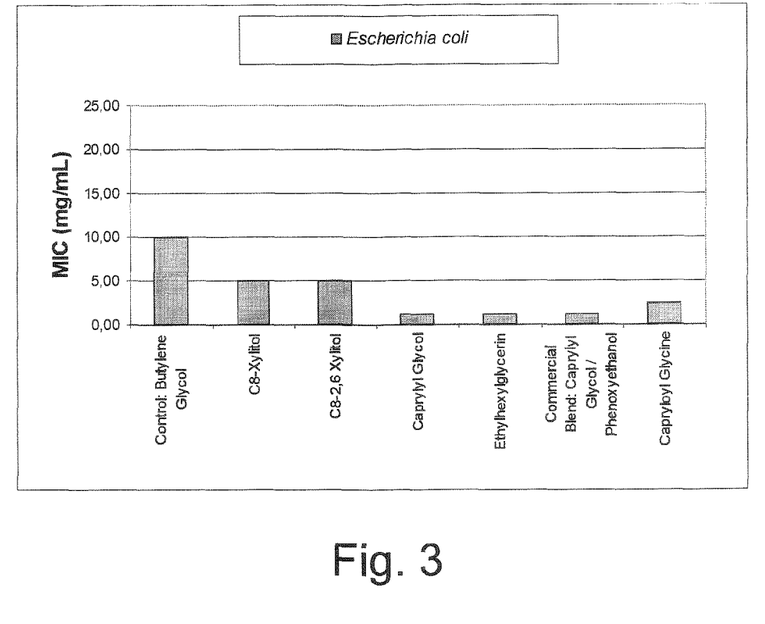
FIG. 3—shows the graph to pure molecule and respective solvent (Control) for *Escherichia coli*
Figure 4:
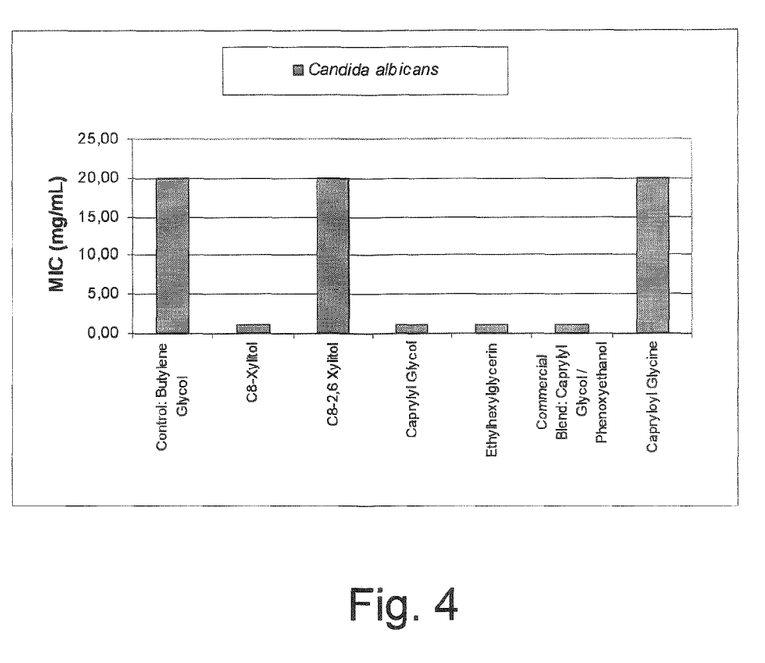
FIG. 4—shows the graph to pure molecule and respective solvent (Control) for *Candida albicans*
Figure 5:
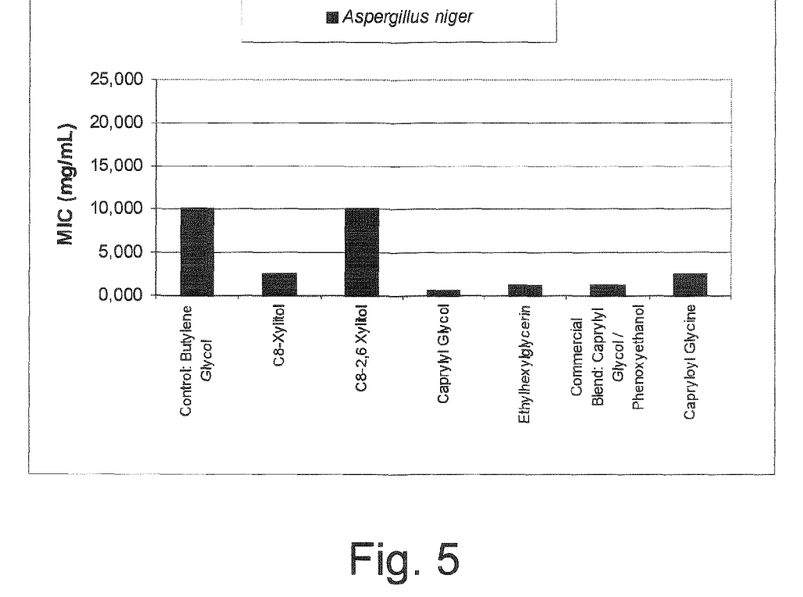
FIG. 5—shows the graph to pure molecule and respective solvent (Control) for *Aspergillus niger*
Figure 6:
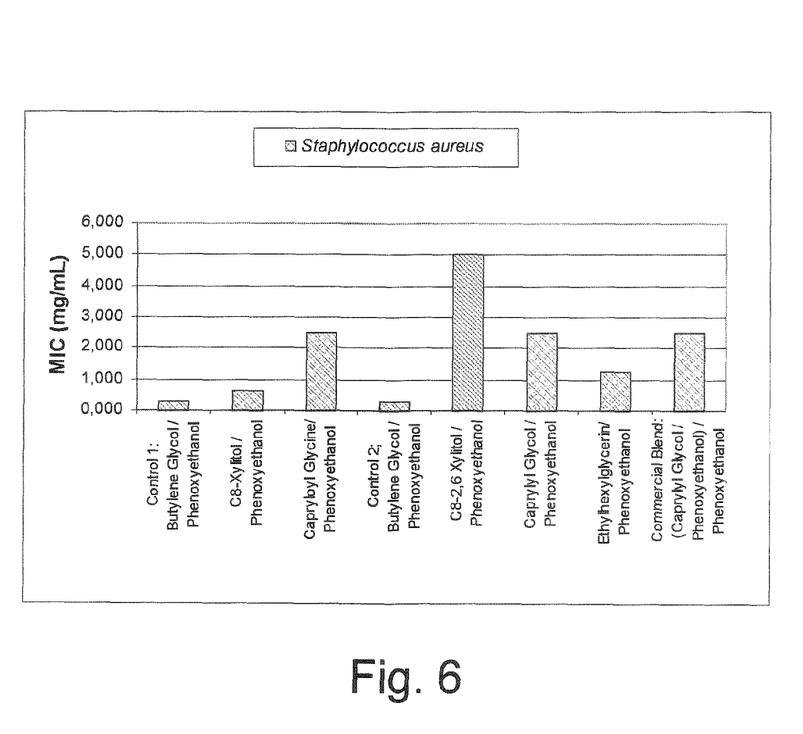
FIG. 6—shows the graph to molecules association with phenoxyethanol and respective solvents (Control 1 and Control 2) for *Staphylococcus aureus*
Figure 7:
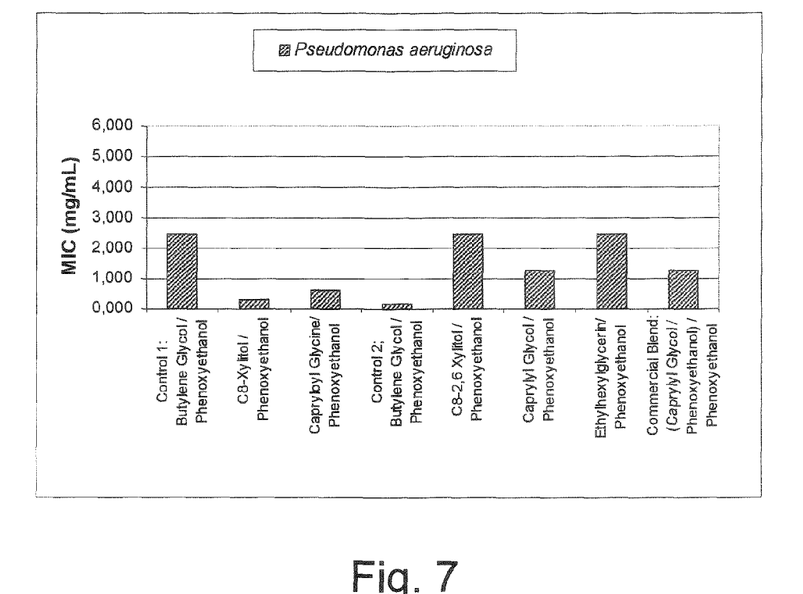
FIG. 7—shows the graph to molecules association with phenoxyethanol and respective solvents (Control 1 and Control 2) for *Pseudomonas aeruginosa*
Figure 8:
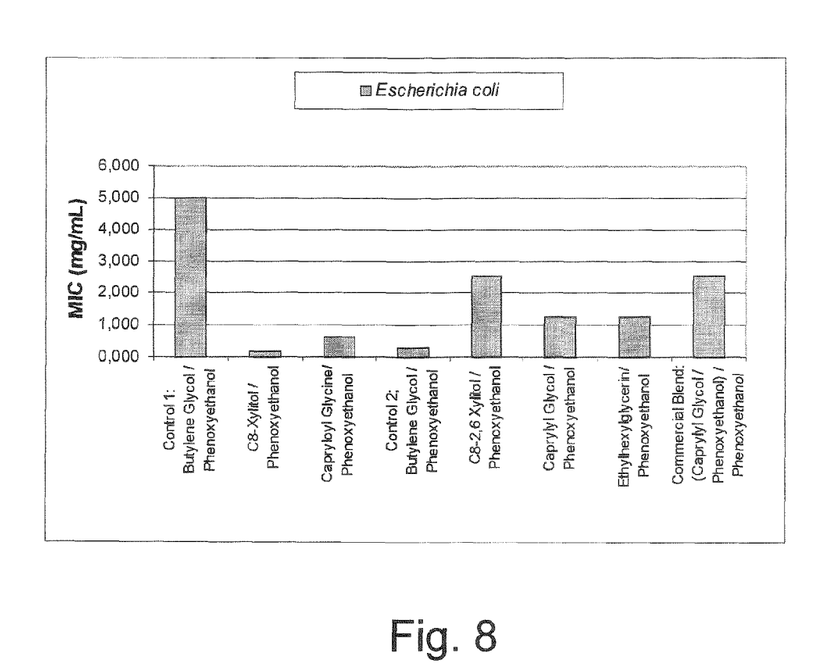
FIG. 8—shows the graph to molecules association with phenoxyethanol and respective solvents (Control 1 and Control 2) for *Escherichia coli*
Figure 9:
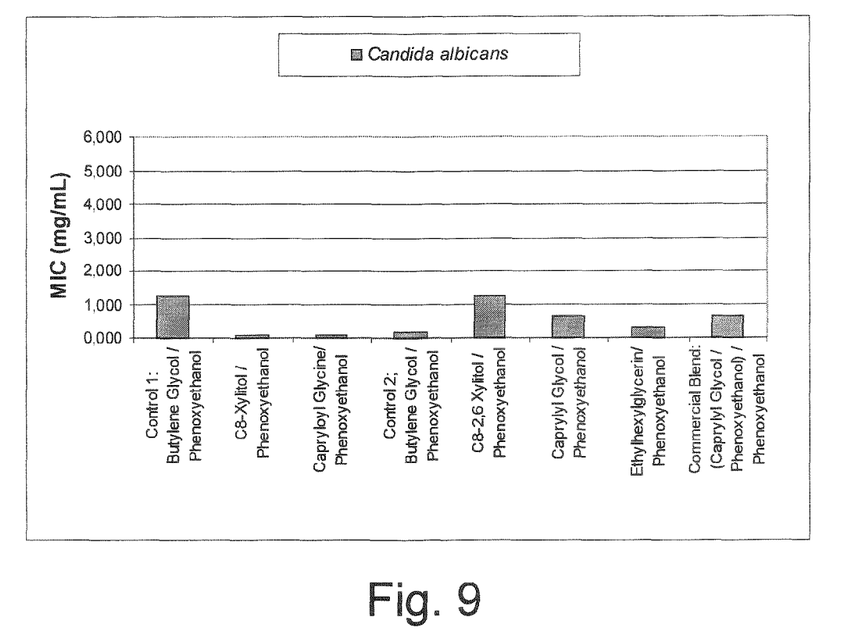
FIG. 9—shows the graph to molecules association with phenoxyethanol and respective solvents (Control 1 and Control 2) for *Candida albicans*
Figure 10:
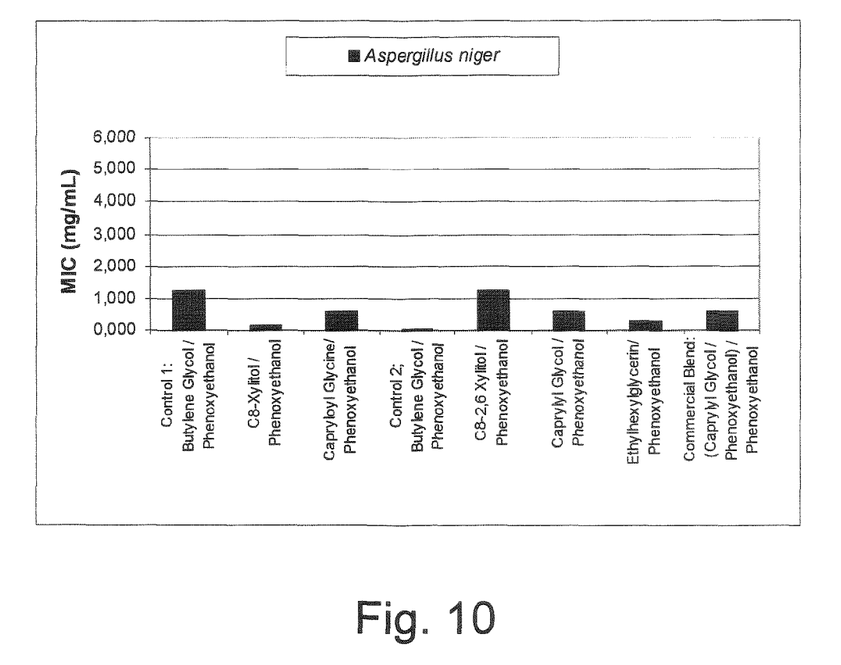
FIG. 10—shows the graph to molecules association with phenoxyethanol and respective solvents (Control 1 and Control 2) for *Aspergillus niger*

The results obtained are described in the represented graphs from 1 to 5 to pure molecules and respective solvent (Control) and from 6 to 10 to molecules association with phenoxyethanol and respective solvents (Control 1 and Control 2).

Conclusion:

The tests were conducted in a comparative way in order to verify that C8-xylitol and C8-2,6 Xylitol molecules is more effective than some molecules with known antimicrobial activity, traditionally used as preservative system.

The results observed on FIGS. 1 to 5 showed that, when compared with other molecules with known antimicrobial activity, C8-Xylitol showed antimicrobial activity against *Candida albicans* similar to Caprylyl Glycol, Ethylhexylglycerin and the commercial association of Caprylyl Glycol and Phenoxyethanol, and better antimicrobial activity than Capryloyl Glycine. The tests with *Staphylococcus aureus* showed that C8-Xylitol has better antimicrobial activity than all molecules evaluated.

It was also possible observe (FIGS. 6 to 10) that, when associated with Phenoxyethanol, C8-Xylitol showed better antimicrobial activity against *Candida albicans* than Caprylyl Glycol, Ethylhexylglycerin and the commercial association of Caprylyl Glycol and Phenoxyethanol, and an antimicrobial activity similar to Capryloyl Glycine. The tests with *Staphylococcus aureus, Pseudomonas aeruginosa, Escherichia coli* and *Aspergillus niger* showed that C8-Xylitol has better antimicrobial activity than all molecules evaluated.

The association of C8-2,6 Xylitol with Phenoxyethanol showed antimicrobial activity against *Pseudomonas aeruginosa* similar to Ethylhexylglycerin and antimicrobial activity against *Escherichia coli* similar to the association of Caprylyl Glycol and Phenoxyethanol.

Based on this result, it was concluded that C8-Xylitol and C8-2,6 Xylitol have the same or better activity as antimicrobial agents than some molecules traditionally used by industries as preservative system, which is a evidence that this molecules could be used as preservative system.

EXAMPLE 2

Determination of the Co-Emulsifier, Emollient/Moisturizing and Solving Properties of the Xylitol Esters Described in this Invention Patent.

This study was conducted using a prototype of xylitol ester, 1-xylitol Palmitate, For this, the product was included in different cosmetic emulsions, in order to assess its emollient/moisturizing, solving and co-emulsifier properties.

A standard formulation was used as an example of stable emulsion, where we conducted the substitution of market agents known as emulsifier, co-emulsifier, emollient/moisturizing and solving with 1-xylitol Palmitate, in order to assess the behavior profile of the xylitol esters as integrants of the formulation.

The results obtained in the used formulation, demonstrating the substitutions for assessing the behavior of the emulsions, are described as follows:

Tests for Assessing the Performance of Xylitol Esters Considering the Following Parameters:

a) Co-emulsifier: association of saccharose esters with high and low H.L.B. and 1-xylitol Palmitate;

b) Low shearing speed (700 r.p.m.);

c) Incorporation into the oily phase;

| MOISTURIZING LOTION 1 | % (w/w) |
|---|---|
| PHASE A | |
| Sucrose Palmitate | 2.50 |
| Sucrose Distearate | 1.50 |
| Cetyl Lactate | 1.50 |
| *Astrocaryum Murumuru* Seed Butter | 1.00 |
| Cetyl Acetate (and) Acetylated Lanolin Alcohol | 1.00 |
| Lanolin Alcohol (and) Mineral Oil | 1.00 |
| Phenoxyethanol (and) parabens | 0.50 |
| PHASE B | |
| Deionized Water q.s. to | 100.00 |
| Disodium EDTA | 0.10 |
| PHASE C | |
| Hydroxyethyl Acrylate (and) Sodium Acryloyldimethyl Taurate Copolymer (and) Squalene (and) Polysorbate 60 | 0.50 |
| PHASE D | |
| Cyclomethicone (and) Dimethicone Crosspolymer | 1.00 |
| Cyclomethicone | 2.00 |

Procedure

Heat, separately, both phases A and B at 75-80° C.

Add phase B to A.

Keep the temperature for 10 minutes under high shear (ULTRA-TURRAX) rate.

Add phase C and start cooling under moderate stirring.

Add phase D at 45° C. Homogenize.

| MOISTURIZING LOTION 2 | % (w/w) |
|---|---|
| PHASE A | |
| 1-XYLITOL PALMITATE | 2.50 |
| Sucrose Distearate | 1.50 |
| Cetyl Lactate | 1.50 |
| Cetearyl Alcohol | 3.00 |
| *Astrocaryum Murumuru* Seed Butter | 1.00 |
| Cetyl Acetate (and) Acetylated Lanolin Alcohol | 1.00 |
| Lanolin Alcohol (and) Mineral Oil | 1.00 |
| Phenoxyethanol (and) parabens | 0.50 |
| PHASE B | |
| Deionized Water q.s. to | 100.00 |
| Disodium EDTA | 0.10 |
| PHASE C | |
| Hydroxyethyl Acrylate (and) Sodium Acryloyldimethyl Taurate Copolymer (and) Squalene (and) Polysorbate 60 | 0.50 |
| PHASE D | |
| Cyclomethicone (and) Dimethicone Crosspolymer | 1.00 |
| Cyclomethicone | 2.00 |

Procedure:

Heat, separately, both phases A and B at 75-80° C.

Add phase B to A.

Keep the temperature for 10 minutes under high shear (ULTRA-TURRAX) rate.

Add phase C and start cooling under moderate stirring.

Add phase D at 45° C. Homogenize.

Results:

|  | Moisturizing Lotion 1 | Moisturizing Lotion 2 |
| --- | --- | --- |
| Initial Viscosity | 48.545 | 57.745 |
| Initial pH | 6.47 | 6.58 |

Conclusion:

According to the results presented in Example 2 (Moisturizing Lotion 1 and 2)-Tests for assessing the performance of the xylitol esters, considering different parameters in each test, we may conclude that the xylitol esters, represented by 1-xylitol palmitate, present excellent co-emulsifier behavior in cosmetic and pharmaceutical emulsions, since they may be used as safe and stable substitute for the esters existing in the market. Also, 1-xylitol palmitate associated to a secondary emulsifier (low HLB) and the consistency agent (alcohol cetoestearilic) presented satisfactory results as primary emulsifier, compared with the saccharose ester with high HLB, which was used as a comparison parameter. Also, in all the emulsion with added 1-xylitol palmitate, was observed an excellent sensorial profile regarding softness, suavity, hydrating and moisturizing of the skin, when compared with the emulsions that did not receive this xylitol ester.

The invention claimed is:

1. A cosmetic preservative composition comprising xylitol esters and ethers associated to chains of fatty acids and alcohols, the esters and ethers being selected from the group consisting of:

wherein R=[H, CH$_3$; —CH$_2$CH$_3$, —CH$_2$(CH$_2$)$_y$—CH$_3$ with y=1 to 15] and n=1-22.

2. The cosmetic preservative composition according to claim 1, wherein the composition also contains at least one compound selected from the group consisting of phenoxyethanol, butylene glycol, glycerin, caprylyl glycol, ethyl hexyl glycerin, phenetyl alcohol, nisin and lactoferrin.

* * * * *

UNITED STATES PATENT AND TRADEMARK OFFICE
CERTIFICATE OF CORRECTION

PATENT NO. : 8,716,506 B2  Page 1 of 1
APPLICATION NO. : 12/998437
DATED : May 6, 2014
INVENTOR(S) : Velazquez Pereda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 6 days.

Signed and Sealed this

Twenty-ninth Day of September, 2015

Michelle K. Lee
*Director of the United States Patent and Trademark Office*